United States Patent
Wen et al.

(10) Patent No.: US 8,618,088 B2
(45) Date of Patent: *Dec. 31, 2013

(54) METHODS OF INHIBITING CHOROIDAL NEOVASCULARIZATION

(75) Inventors: Rong Wen, Bala Cynwyd, PA (US); Zhijun Luo, Chestnut Hill, MA (US); Alan M. Laties, Philadelphia, PA (US)

(73) Assignee: University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/433,739

(22) Filed: Mar. 29, 2012

(65) Prior Publication Data
US 2012/0190705 A1  Jul. 26, 2012

Related U.S. Application Data

(63) Continuation of application No. 10/665,203, filed on Sep. 18, 2003, now Pat. No. 8,163,726.

(60) Provisional application No. 60/412,088, filed on Sep. 18, 2002.

(51) Int. Cl.
*A61K 31/436* (2006.01)
*A61K 31/445* (2006.01)

(52) U.S. Cl.
USPC .......................................... 514/185; 514/912

(58) Field of Classification Search
USPC .................................. 514/185, 912
See application file for complete search history.

(56) References Cited

U.S. PATENT DOCUMENTS

| | | | |
|---|---|---|---|
| 5,011,844 A | 4/1991 | Fehr | |
| 5,078,999 A | 1/1992 | Warner et al. | |
| 5,100,899 A | 3/1992 | Calne | |
| 5,189,042 A | 2/1993 | Goulet et al. | |
| 5,192,773 A | 3/1993 | Armistead | |
| 5,258,389 A | 11/1993 | Goulet et al. | |
| 5,368,865 A | 11/1994 | Asakura et al. | |
| 5,378,475 A | 1/1995 | Smith et al. | |
| 5,387,589 A * | 2/1995 | Kulkarni | 514/291 |
| 5,457,111 A | 10/1995 | Luly et al. | |
| 5,514,686 A | 5/1996 | Mochizuki | |
| 5,516,770 A | 5/1996 | Waranis et al. | |
| 5,527,907 A | 6/1996 | Or et al. | |
| 5,530,006 A | 6/1996 | Waranis et al. | |
| 5,532,248 A | 7/1996 | Goulet et al. | |
| 5,559,121 A | 9/1996 | Harrison et al. | |
| 5,601,844 A | 2/1997 | Kagayama et al. | |
| 5,616,588 A | 4/1997 | Waranis et al. | |
| 5,621,108 A | 4/1997 | Smith, III et al. | |
| 5,672,605 A | 9/1997 | Or et al. | |
| 5,773,019 A | 6/1998 | Ashton et al. | |
| 5,800,807 A | 9/1998 | Hu et al. | |
| 5,883,082 A | 3/1999 | Bennett et al. | |
| 6,015,815 A * | 1/2000 | Mollison | 514/291 |
| 6,254,860 B1 | 7/2001 | Garst | |
| 6,329,386 B1 | 12/2001 | Mollison | |
| 6,376,517 B1 | 4/2002 | Ross et al. | |
| 6,387,918 B1 | 5/2002 | Yamanaka et al. | |
| 6,399,629 B1 | 6/2002 | Chamberland et al. | |
| 6,440,990 B1 | 8/2002 | Cottens et al. | |
| 6,482,802 B1 | 11/2002 | Hu et al. | |
| 6,534,693 B2 | 3/2003 | Fischell et al. | |
| 6,576,224 B1 | 6/2003 | Osbakken et al. | |
| 6,579,901 B2 | 6/2003 | Chen et al. | |
| 6,632,836 B1 | 10/2003 | Baker et al. | |
| 6,699,493 B2 | 3/2004 | Wong | |
| 6,713,081 B2 | 3/2004 | Robinson et al. | |
| 6,812,220 B2 | 11/2004 | Jackson et al. | |
| 6,872,383 B2 | 3/2005 | Ueno | |
| 6,890,546 B2 | 5/2005 | Mollison et al. | |
| 2002/0123505 A1 | 9/2002 | Mollison et al. | |
| 2003/0018044 A1 | 1/2003 | Peyman | |
| 2003/0027744 A1 | 2/2003 | Dana | |
| 2003/0031631 A1 | 2/2003 | Osbakken et al. | |
| 2003/0069560 A1 | 4/2003 | Adamis et al. | |
| 2003/0077297 A1 | 4/2003 | Chen et al. | |
| 2003/0190286 A1 | 10/2003 | Dugger et al. | |
| 2004/0018228 A1 | 1/2004 | Fischell et al. | |
| 2004/0057958 A1 | 3/2004 | Waggoner et al. | |
| 2004/0092435 A1 | 5/2004 | Peyman | |
| 2004/0167152 A1 | 8/2004 | Rubio et al. | |
| 2004/0234611 A1 | 11/2004 | Ahlheim et al. | |

(Continued)

FOREIGN PATENT DOCUMENTS

| | | |
|---|---|---|
| EP | 0041745 | 12/1981 |
| EP | 0041795 B1 | 1/1985 |

(Continued)

OTHER PUBLICATIONS

Whiting, P.H., et al., "The effect of rapamycin on renal function in the rat: a comparative study with cyclosporine", Toxicology Letters, vol. 58, No. 2, Oct. 1, 1991, pp. 169-179.

(Continued)

*Primary Examiner* — Zohreh Fay
(74) *Attorney, Agent, or Firm* — Knobbe Martens Olson & Bear LLP

(57) ABSTRACT

The present invention relates to compositions and methods for inhibiting unwanted angiogenesis, particularly those of ocular tissues. The treatment, inhibition, and/or prevention of choroidal neovasculature (CNV) is provided, along with an animal model for CNV and imaging techniques that permit the screening of potential agents as anti-angiogenesis and anti-CNV agents.

21 Claims, 3 Drawing Sheets

(56) References Cited

U.S. PATENT DOCUMENTS

| | | |
|---|---|---|
| 2005/0025810 A1 | 2/2005 | Peyman |
| 2005/0048123 A1 | 3/2005 | Su et al. |
| 2005/0123605 A1 | 6/2005 | Hunter et al. |

FOREIGN PATENT DOCUMENTS

| | | |
|---|---|---|
| EP | 0650730 A1 | 5/1995 |
| JP | 05-194212 | 8/1993 |
| JP | 2002-522485 | 7/2002 |
| WO | WO 93/19763 | 10/1993 |
| WO | WO 94/21642 | 9/1994 |
| WO | WO 96/41865 | 12/1996 |
| WO | WO 97/10806 | 3/1997 |
| WO | WO 97/16068 | 5/1997 |
| WO | WO 99/20261 | 4/1999 |
| WO | WO 99/22722 | 5/1999 |
| WO | WO 99/34830 | 5/1999 |
| WO | WO 99/37667 | 7/1999 |
| WO | WO 99/58126 | 11/1999 |
| WO | WO 00/09109 | 2/2000 |
| WO | WO 00/28945 | 5/2000 |
| WO | WO 00/38703 | 7/2000 |
| WO | WO 00/40089 | 7/2000 |
| WO | WO 01/30386 | 5/2001 |
| WO | WO 01/42219 | 6/2001 |
| WO | WO 01/47495 | 7/2001 |
| WO | WO 01/60345 | 8/2001 |
| WO | WO 02/28387 | 4/2002 |
| WO | WO 02/062335 | 8/2002 |
| WO | WO 02/074196 | 9/2002 |
| WO | WO 03/068186 | 8/2003 |
| WO | WO 03/074027 | 9/2003 |
| WO | WO 03/074029 | 9/2003 |
| WO | WO 03/090684 | 11/2003 |
| WO | WO 03/092671 | 11/2003 |
| WO | WO 2004/019904 | 3/2004 |
| WO | WO 2004/027027 | 4/2004 |
| WO | WO 2004/028477 | 4/2004 |
| WO | WO 2004/043480 | 5/2004 |
| WO | WO 2004/074445 | 9/2004 |
| WO | WO 2005/011813 A2 | 2/2005 |
| WO | WO 2005/051452 | 6/2005 |

OTHER PUBLICATIONS

"Retinal Disorders", in: M.H. Beers, R. Berkow: "The Merck manual of Diagnosis and Therapy—Seventeenth Edition", 1999, Merck Research Laboratories, Whitehouse Station, N.J., XP002685262, pp. 731-731, col. 1, last paragraph—col. 2, paragraph 4.

Wen, R., et al., "Rapamycin Inhibits Choroidal Neovascularization", Invest Ophthalmol Vis Sci, vol. 44, 2003, E-Abstract 3928.

U.S. Appl. No. 60/503,840, Cooper, et al.

Akselband, et al. "Rapamycin Inhibits Spontaneous and Fibroblast Growth Factor Beta-Stimulated Proliferation of Endothelial Cells and Fibroblasts" Transplantation Proceedings, vol. 23, No. 6. Dec. 1991:p. 2833-2836.

Auricchio, et al. "Pharmacological Regulation of Protein Expression from Adeno-Associated Viral Vectors in the Eye" Molecular Therapy, Jul. 1, 2002, p. 238-242.

Bainbridge, et al. "Hypoxia-regulated transgene expression in experimental retinal and choroidal neovascularization." Gene Therapy. 2003:p. 1049-1054.

Guba, et al. "Rapamycin inhibits tumor growth and metastasis by antiangiogenesis" Chirurgisches Forum 2001. May 1, 2001: p. 37-39.

Guba, et al. "Rapamycin inhibits primary and metastatic tumor growth by antiangiogenesis: involvement of vascular endothelial growth factor." Nature Medicine. vol. 8. No. 2. Feb. 2002. p. 128-135.

Hackstein et al., "Rapamycin inhibits macropinocytosis and mannose receptor—mediated . . . ", *Blood*; vol. 100 No. 3 (1084-1087), Aug. 2002.

Humar, et al. "Hypoxia enhances vascular cell proliferation and angiogenesis in vitro via rapamycin (mTOR)—dependent signaling." The FASEB Journal. vol. 16. Jun. 2002: p. 771-780.

Hikita, Naofumi, Journal of the Kurume Medical Association, Jan. 1994, vol. 57, No. 1, pp. 176-189, Japan (In Japanese; relevance is citation in Japanese Office Action).

Kimura, Hideya, Angiogenesis Inhibitors, Atarashii Ganka (New Ophthalmology), Jul. 30, 2001, vol. 18, No. 7, pp. 867-870, Japan (In Japanese; relevance is citation in Japanese Office Action).

Kuroki, et al. "Rapamycin Inhibits Retinal and Choroidal Neovascularization in Mice." ARVO 2003 Abstract No. 573. May 4, 2003.

Marsland. "The macrolide immunosuppressants in dermatology: mechanisms of action." Eur. J Dermatol. Nov.-Dec. 2002. p. 618-22.

Olsen, et al. "Rapamycin Inhibits Corneal Allograft Rejection and Neovascularization," Arch. Ophthalmol, vol. 112, pp. 1471-1475, Nov. 1994.

Renau, et al., "Conformationally-Restricted Analogues of Efflux Pump Inhibitors that Potentiate the Activity of Levofloxacin in *Pseudomonas aeruginosa*." Bioorganic& Med. Chem. Letters. (2003) 13:2755-2758.

Renau, et al. "Addressing the Stability of C-Capped Dipeptide Efflux Pump Inhibitors that Potentiate the Activity of Levofloxacin in *Pseudomonas aeruginosa*." Bioorganic & Med. Chem. Letters. (2001) 11:663-667.

Rivera et al., "Long-term regulated expression of growth hormone in mice after intramuscular gene transfer," *PNAS*; vol. 96: 8657-8662, Jul. 1999.

Shen, et al. "Combined Effect of Cyclosporine and Sirolimus on Improving the Longevity of Recombinat Adenovirus-Mediated Transgene Expression in the Retina." Arch Ophthalol. Jul. 2001. vol. 119. p. 1033-1043.

Simamora, P. et al., "Solubilization of Rapamycin," *Int. J. Pharm.* 213:25-29, Feb. 1, 2001.

Sloper, et al., Tacrolimus (FK506) in the Treatment of Posterior Uveitis Refractory to Cyclosporine, Ophthalmology, Apr. 1999, pp. 723-728, vol. 106, No. 4.

Stepkowski et al., "Rapamycin, a potent immunosuppressive drug for vascularized heart, kidney, and small bowel transplantation in the rat," *Transplantation*, vol. 51:22-26, Jan. 1991.

"Study of possible anticancer drug reveals new mechanism of gene regulation." NewsRx. Jan. 14, 2003.

Treins, et al. "Insulin Stimulates Hypoxia-inducible Factor 1 through a Phosphatidylinositol 3-Kinase/Target of Rapamycin-dependent Signaling Pathway." Journal of Biological Chemistry, Aug. 2, 2002. vol. 277, No. 31 p. 27975-27981.

Wen, et al. "Rapamycin Inhibits Choroidal Neovascularization" ARVO 2003. Abstract No. 3928 May 7, 2003.

Zubilewicz, et al., Two Distinct Signalling Pathways are Involved in FGF2-Stimulated Proliferation of Choriocapillary Endothelial Cells: A Comparative Study With VEGF, Mar. 22, 2001, vol. 20, No. 12, pp. 1403-1413.

Canadian Intellectual Property Office—Office Action, Application No. 2,498,191, dated May 6, 2010.

Canadian Intellectual Property Office—Office Action, Application No. 2,498,191, dated Mar. 15, 2011.

EPO Supplementary Partial European Search Report, for EP Application No. EP 03 75 4653; dated Jul. 18, 2008.

EPO—Invitation to Correct Deficiencies, Application No. 03 754 653.8-1216, dated Jun. 25, 2010.

EPO—Second Examination Report, Application No. 03 754 653.8-1216, dated Mar. 30, 2012.

Japanese Patent Office Action, Patent Application No. 2004-537893, Mailing Date Sep. 29, 2009 (English Translation).

Japanese Patent Office Action, Patent Application No. 2010-223994, Mailing Date Jan. 8, 2013 (English Translation).

JWB Bainbridge et al., "Gene therapy progress and prospects: the eye", Gene Therapy, vol. 13, No. 16, Aug. 1, 2006, pp. 1191-1197.

Anonymous: "Dry AMD", AMD.org Macular degeneration partnership, retrieved from the Internet: URL:http://www.amd.org/what-is-amd/dry-amd.html. Retrieved on Jul. 10, 2013.

Communication Pursuant to Article 94(3) EPC dated Jul. 23, 2013 in European Application No. 12004712.1.

\* cited by examiner

METHODS OF INHIBITING CHOROIDAL NEOVASCULARIZATION

RELATED APPLICATION

This application is a continuation of application Ser. No. 10/665,203, filed Sep. 18, 2003, which issued on Apr. 24, 2012 as U.S. Pat. No. 8,163,726 B2, which is a nonprovisional application of and claims priority to U.S. Provisional Application No. 60/412,088, filed on Sep. 18, 2002, each of which is incorporated herein by reference in its entirety.

GOVERNMENT INTERESTS

This invention was supported in part by Grant Nos. Y12727 from the U.S. National Institutes of Health. The Government may have certain rights in this invention.

TECHNICAL FIELD

The present invention relates to compositions and methods for inhibiting unwanted angiogenesis, including that of ocular tissues. In particular, compositions and methods for the treatment of choroidal neovasculature (CNV) in ocular diseases are provided. While the invention is exemplified with respect to rapamycin (sirolimus) and tacrolimus, the invention provides for the use of the family of "limus" compounds to inhibit unwanted angiogenesis.

BACKGROUND OF THE INVENTION

The retina of the eye contains the cones and rods that detect colors. In the center of the retina is the macula lutea, which is about ⅓ to ½ cm in diameter. The macula provides detailed vision, particularly in the center (the fovea), because the cones are higher in density. Blood vessels, ganglion cells, inner nuclear layer and cells, and the plexiform layers are all displaced to one side (rather than resting above the cones), thereby allowing light a more direct path to the cones.

Under the retina are the choroid, comprising a collection of blood vessels embedded within a fibrous tissue, and the deeply pigmented epithelium, which overlays the choroid layer. The choroidal blood vessels provide nutrition to the retina (particularly its visual cells).

There are a variety of retinal disorders, whose current treatment is not optimal. The retina may tear, form holes and separate from the underlying choroid.

Age-related macular degeneration (AMD) is the major cause of severe visual loss in the United States for individuals over the age of 55. AMD occurs in either an atrophic or (less commonly) an exudative form. In exudative AMD, blood vessels grow from the choriocapillaris through defects in Bruch's membrane, and in some cases the underlying retinal pigment epithelium (choroidal neovascularization or angiogenesis). Organization of serous or hemorrhagic exudates escaping from these vessels results in fibrovascular scarring of the macular region with attendant degeneration of the neuroretina, detachment and tears of the retinal pigment epithelium, vitreous hemorrhage and permanent loss of central vision. This process is responsible for more than 80% of cases of significant visual loss in patients with AMD.

Several studies have recently described the use of laser photocoagulation in the treatment of initial or recurrent neovascular lesions associated with AMD (Macular Photocoagulation Study Groups (1991) in *Arch. Ophthal.* 109:1220; *Arch. Ophthal.* 109:1232; *Arch Ophthal.* 109:1242). Unfortunately, AMD patients with subfoveal lesions subjected to laser treatment experienced a rather precipitous reduction in visual acuity (mean 3 lines) at 3 months follow-up. Moreover, at two years post-treatment treated eyes had only marginally better visual acuity than their untreated counterparts (means of 20/320 and 20/400, respectively). Another drawback of the procedure is that vision after surgery is immediately worse.

Choroidal neovascularization (CNV) has proven recalcitrant to treatment in most cases. Laser treatment can ablate CNV and help to preserve vision in selected cases not involving the center of the retina, but this is limited to only about 10% of the cases. There is no other treatment available to correct CNV. Unfortunately, even with successful laser photocoagulation, the neovascularization recurs in about 50-70% of eyes (50% over 3 years and >60% at 5 years). (Macular Photocoagulation Study Group, *Arch. Ophthalmol.* 204:694-701 (1986)). In addition, many patients who develop CNV are not good candidates for laser therapy because the CNV is too large for laser treatment, or the location cannot be determined so that the physician cannot accurately aim the laser. Thus, until the present invention, there has been a long-felt need for methods that will prevent or significantly inhibit choroidal neovascularization.

In addition to AMD, choroidal neovascularization is caused by such retinal disorders as: presumed ocular histoplasmosis syndrome, myopic degeneration, angioid streaks and ocular trauma. Angiogenic damage associated with retinal and intravitreal neovascularization occurs in a wide range of disorders including diabetic retinopathy, venous occlusions, sickle cell retinopathy, retinopathy of prematurity, retinal detachment, ocular ischemia and trauma.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

DISCLOSURE OF THE INVENTION

The present invention provides compositions and methods that are effective in inhibiting unwanted angiogenesis, specifically choroidal neovascularization (CNV) that is associated with ocular diseases such as age related macular degeneration (AMD) and histoplasmosis syndrome. Compositions of the invention for inhibiting angiogenesis comprise active agents in the "limus" family of compounds, which bind to members of the immunophilin family of cellular proteins, including cyclophilins and FK506-binding proteins (FKBPs), to inhibit angiogenesis in choroidal membranes. Non-limiting members of the "limus" family of compounds include sirolimus (rapamycin) and its water soluble analog SDZ-RAD, tacrolimus, everolimus, pimecrolimus, CCI-779 (Wyeth), AP23841 (Ariad), and ABT-578 (Abbott Laboratories) as well as analogs and derivatives thereof.

A therapeutic amount of the active agents of the invention may be administered to a patient by a variety of different routes and can be given in dosages that are safe and provide angiogenic inhibition at internal sites. The present invention thus provides methods of treating mammalian diseases characterized by undesired and uncontrolled angiogenesis by administering a composition comprising one or more active agents of the invention. In a particular embodiment of the invention, methods to inhibit or treat choroidal neovascularization (CNV) of the eye are provided.

Thus, the present invention is especially useful for treating certain ocular neovascular diseases such as macular degeneration, including age-related macular degeneration (AMD).

The invention is particularly useful in the treatment or inhibition of the wet form of AMD wherein blood vessels grow from their normal location in the choroids into an undesirable position under the retina. Leakage and bleeding from these new blood vessels results in vision loss and possibly blindness. The invention also provides methods for inhibiting the transition from the dry form of AMD (wherein the retinal pigment epithelium or RPE degenerates and leads to photoreceptor cell death and the formation of yellow deposits called drusen under the retina) to the wet form of AMD. The invention thus also provides methods for the treatment of the dry form of AMD.

Compounds which are contemplated for use in the present invention are administered to the patient to halt the progression of the disease and permit reductions in, or regression of, the neovascularization. Other diseases that can be treated using the present invention include, but are not limited to, diabetic retinopathy, neovascular glaucoma and retrolental fibroplasia.

Accordingly, and in a first aspect, the invention provides compounds, compositions, kits and methods to inhibit unwanted angiogenesis as well as neovascularization in the retina of a human or animal. In a second aspect, the invention provides a treatment for diseases mediated by angiogenesis or choroidal neovascularization in a subject. In a further aspect, the invention provides methods for preventing, inhibiting or treating the wet form of AMD, including inhibiting the loss of vision associated therewith.

Another aspect of the invention is the use of the above described methods in combination with other methods known for the treatment of angiogenesis, neovascularization, and the wet form of AMD as well as reducing the loss of visual acuity associated therewith. Moreover, the invention provides methods for the visualization of blood vessels by use of lipophilic dyes in a body as well as an animal model for choroidal neovascularization that can be applied as an assay for rapid identification of additional anti-angiogenic, anti-neovascularization, and anti-AMD compounds.

Advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE DRAWINGS

FIG. 3 shows inhibition of CNV formation by rapamycin. Scale bar: 100 μm.

DETAILED DESCRIPTION OF PREFERRED EMBODIMENTS OF INVENTION

Figure 1:
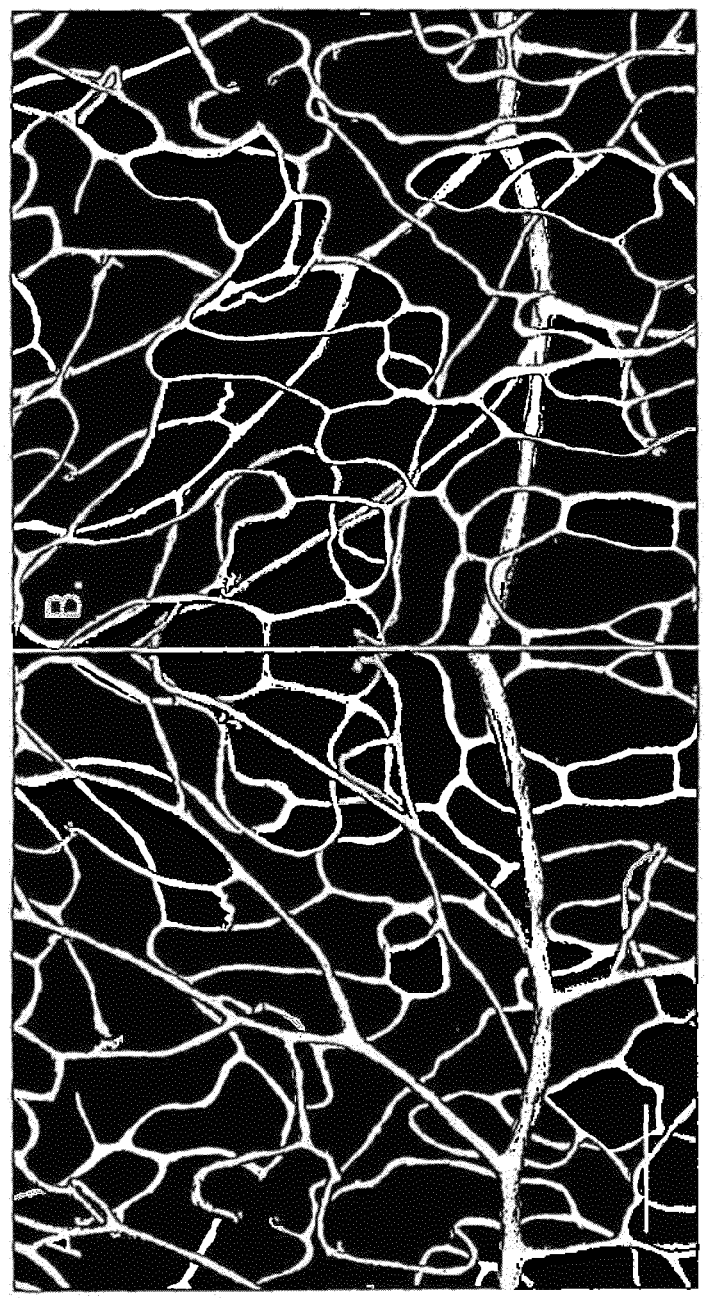
FIG. 1 shows a three dimensional reconstruction of retinal blood vessels. Scale bar: 100 μm.

The invention provides methods for the treatment of disorders involving angiogenesis and neovascularization, including ophthalmic disorders, and in particular retinal disorders involving macular degeneration, choroidal neovascularization, and the like in the retina or between the retina and its underlying choroidal tissue, or involving choroidal tissue, as described above. The methods comprise a novel use for the immune suppressor, rapamycin, which is also known as macrocyclic lactone sirolimus (commercially available as Rapamune®, Wyeth-Ayerst) (See, Physician's Desk Reference, 55.sup.th edition). According to the Merck Index, 12.sup.th edition, Rapamune is also known as RAPA, RPM, sirolimus, AY22989, and NSC-226080.

Although Sirolimus is known as an immunosuppressant, it has been reported as an anti-angiogenic compound in the context of primary and metastatic tumors (Guba et al., Nature Medicine 18(2):128-135 (February 2002) and Guba et al., Chir. Forum Exp. Klin. Forsch. Band 30, pages 37-39 (2001)). In those studies, there is no discussion related to other types of neovascularization, such as choroidal neovascularization. Instead, there is a discussion of the involvement of vascular endothelial growth factor (VEGF) and the serum levels thereof. VEGF is a factor implicated in numerous indications without certainty that therapies directed thereto are efficacious in treating said indications. For example, VEGF has been suggested as involved in the formation of pathogenic new vessels in AMD, although VEGF activity has never been tested in an animal model with regard to AMD. Therefore, the ability to treat AMD by targeting VEGF activity remains experimental.

In addition to the use of sirolimus, the invention provides for the use of other immunophilin binding compounds as well as rapamycin derivatives and analogs to treat angiogenesis and neovascularization. Non-limiting examples of such compounds include SDZ-RAD, tacrolimus, everolimus, pimecrolimus, CCI-779 (Wyeth), AP23841 (Ariad), and ABT-578 (Abbott Laboratories) as well as those described in U.S. Pat. Nos. 5,527,907; 6,376,517; and 6,329,386. Additional derivatives include those disclosed in published U.S. Patent application 2002/0123505. All of these documents are hereby incorporated by reference as if fully set forth.

The invention also provides for the use of the above agents in combination with other agents and therapies for the treatment of angiogenesis or neovascularization, particularly CNV. Non-limiting examples of such additional agents and therapies include pyrrolidine, dithiocarbamate (NF.kappa.B inhibitor); squalamine; TPN 470 analogue and fumagillin; PKC (protein kinase C) inhibitors; Tie-1 and Tie-2 kinase inhibitors; inhibitors of VEGF receptor kinase; proteasome inhibitors such as Velcade™ (bortezomib, for injection; ranibizumab (Lucentis™) and other antibodies directed to the same target; pegaptanib (Macugen™); vitronectin receptor antagonists, such as cyclic peptide antagonists of vitronectin receptor-type integrins; .alpha.-v/.beta.-3 integrin antagonists; .alpha.-v/.beta.-1 integrin antagonists; thiazolidinediones such as rosiglitazone or troglitazone; interferon, including .gamma.-interferon or interferon targeted to CNV by use of dextran and metal coordination; pigment epithelium derived factor (PEDF); endostatin; angiostatin; anecortave acetate; acetonide; triamcinolone; tetrathiomolybdate; RNA silencing or RNA interference (RNAi) of angiogenic factors, including ribozymes that target VEGF expression; Accutane™ (13-cis retinoic acid); ACE inhibitors such as quinapril or perindopril; inhibitors of mTOR (mammalian target of rapamycin); 3-aminothalidomide; pentoxifylline; 2-methoxyestradiol; colchicines; AMG-1470; cyclooxygenase inhibitors such as nepafenac, rofecoxib, and diclofenac; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; Visudyne™ and other photosensitizers with photodynamic therapy (PDT); and laser photocoagulation.

"Macular degeneration" is characterized by the excessive buildup of fibrovascular deposits in or beneath the macula and retina and the atrophy and/or dislodgement of the retinal pigment epithelium (RPE). The administration of rapamycin appears to limit excessive angiogenesis, such as choroidal neovascularization in age-related macular degeneration (AMD), which may occur without such treatment. As used herein, the term "angiogenesis" means the generation of new blood vessels ("neovascularization") into a tissue or organ. An "angiogenesis-mediated disease or condition" of the eye or retina is one in which new blood vessels are generated in a pathogenic manner in the eye or retina, resulting in loss of vision or other problem, e.g., choroidal neovascularization associated with AMD.

The methods of the invention include a preferred embodiment using rapamycin and/or other active agents in vitro or in vivo. When administered in vitro, the method is used, for example, to screen for, or assay the effects of, additional candidate active agents for the activity of controlling or reducing neovascularization or angiogenesis in retinal or choroidal tissue or cells. This may be used as a helpful assay for additional anti-angiogenesis or CNV agents. When administered in vivo the method is used, for example, to treat a patient having a predisposition to develop the choroidal neovascularization typically seen in AMD, or to prevent or inhibit choroidal neovascularization in such a patient, or to reduce choroidal neovascularization in an AMD patient. Prevent, inhibit and reduce are given their ordinary meanings with regard to the effect of the active agents of the invention on choroidal neovascularization. A patient having a predisposition or in need of prevention may be identified by the skilled practitioner by established methods and criteria in the field. The skilled practitioner may also readily diagnose individuals as in need of inhibition or treatment based upon established criteria in the field for identifying unwanted angiogenesis and/or neovascularization.

An effective amount of the drug is that amount which provides the therapeutic effect sought, e.g., an therapeutically effective dose of rapamycin or drug equivalent would be the amount which reduces choroidal neovascularization in an AMD patient, or which inhibits or completely prevents choroidal neovascularization in a patient predisposed to AMD, or who, even without predisposition, shows early signs of AMD. Thus, the therapeutically effective dose may not be the same in every patient treated with rapamycin. An effective amount also refers to the amount of drug which inhibits angiogenesis or neovascularization in a model or assay therefor, such as that disclosed by the present invention.

"Patient" preferably refers to a subject who has, or who may develop, choroidal neovascularization associated with exudative AMD unless treated by the preferred methods of the present invention. Such a patient is preferably a mammal, more preferably a human, although the present methods are also application to model experimental animals and veterinary animal subjects.

An active agent of the invention, such as rapamycin, is preferably administered orally, intravenously, topically, intraocularly, intramuscularly, locally or in an ocular device. More preferably the mode of administration is selected from the following: intraocular injection, subretinal injection, subscleral injection, intrachoroidal injection, subconjunctival injection, topical administration, oral administration and parenteral administration. Most preferably the active agent is directly administered to the retinal area by subretinal injection, although less invasive modes of administration may be developed that are equally as effective. Formulations for timed release or delayed release over time are also provided by the present invention.

The dosage of the active agent will depend on the condition being treated, the particular agent, and other clinical factors such as weight and condition of the human or animal and the route of administration of the agent. It is to be understood that the present invention has application for both human and veterinary use. For administration to humans, an effective dosage is one that inhibits choroidal neovascularization. In the case of rapamycin, an inhibiting amount that can be employed ranges generally between about 0.1 to 300 mg/kg/day, preferably between approximately 0.5 and 50 mg/kg/day, and most preferably between approximately 1 to 10 mg/kg/day. Dosages of various agents of the invention for treating various conditions can be refined by the use of clinical trials on the present invention. Additionally, dose ranges for the practice of the invention include those disclosed in U.S. Pat. Nos. 6,376,517 and 5,387,589, which are hereby incorporated by reference as if fully set forth.

An active agent of the invention, such as rapamycin, may be subjected to conventional pharmaceutical operations, such as sterilization and/or may contain conventional adjuvants, such as preservatives, stabilizers, wetting agents, emulsifiers, buffers etc. The agents may also be formulated with pharmaceutically acceptable excipients for clinical use to produce a pharmaceutical composition. Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc. Stated differently, the active agents of the invention may be used to prepare a medicament for the treatment of any of the conditions described herein.

For administration, an active agent such as rapamycin may be combined with one or more adjuvants appropriate for the indicated route of administration. The active agent may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art and may be used in the practice of the invention. The carrier or diluent may include time delay material, such as glyceryl monostearate or glyceryl distearate alone or with a wax, or other materials well known in the art.

The formulations of the invention include those suitable for oral, ophthalmic, (including intravitreal or intracameral) nasal, topical (including buccal and sublingual), or parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Further provided in another aspect of the invention is a pharmaceutical composition comprising: a therapeutically effective amount of an active agent of the invention, such as rapamycin, and a pharmaceutically acceptable carrier suitable for administration to the eye or eye tissue.

In addition, a kit is provided, comprising at least one vial comprising a therapeutically effective amount of an active agent of the invention, such as rapamycin, and a second vial comprising a pharmaceutically acceptable carrier suitable for administration to the eye or eye tissue. Other kits of the invention comprise components such as the active agent of the invention for use in the practice of the methods disclosed herein, wherein containers, each with one or more of the various reagents (typically in concentrated form) utilized in the methods, including, for example, buffers and other reagents as necessary, are also included. A label or indicator describing, or a set of instructions for use of, kit components in a method of the present invention, will also be typically included, where the instructions may be associated with a package insert and/or the packaging of the kit or the components thereof.

Diseases associated with retinal/choroidal neovascularization that can be treated according to the present invention include, but are not limited to, diabetic retinopathy, macular degeneration, retinopathy of prematurity, infections causing a retinitis or choroiditis, presumed ocular histoplasmosis, myopic degeneration, angioid streaks, ocular trauma, and AMD. Other non-limiting examples of diseases and unwanted conditions that may be treated with the present invention include, but are not limited to, pseudoxanthoma elasticum, vein occlusion, artery occlusion, carotid obstructive disease, Sickle Cell anemia, Eales disease, myopia, chronic retinal detachment, hyperviscosity syndromes, toxoplasmosis, trauma and post-laser complications. Other diseases include, but are not limited to, diseases associated with rubeosis (neovascularization of the angle) and diseases caused by the abnormal proliferation of fibrovascular or fibrous tissue, including all forms of proliferative vitreoretinopathy, whether or not associated with diabetes.

In addition to the compositions and methods for the treatment of unwanted conditions, the invention also provides methods for the visualization of blood vessels in a body. Such methods may also be viewed as methods of detectably labeling blood vessels in a body for subsequent visualization. Conventional ways to process tissue samples for blood vessel visualization are both labor intensive and time consuming. To improve the efficiency in tissue preparation, a technique called Vessel Painting is provided by the present invention. The basic concept of Vessel Painting is to selectively stain the inner lining of blood vessels with fluorescent dye. Blood vessels are lined with endothelial cell membrane, a lipid bilayer membrane that can be stained directly with a lipophilic dye. The key to this technique is a specially formulated solution, the Vessel Paint, which contains a lipophilic dye. Non-limiting examples of such dyes are available from Molecular Probes, and they include DiI, DiO, DiO, DiD, DiA, and DiR, which are long-chain dialkylcarbocyanines and dialkylaminostyryl dyes used as neuronal tracers. By intracardiac perfusion of an animal with Vessel Paint followed by a wash, optionally in a fixative solution such as, but not limited to 4% paraformaldehyde solution, blood vessels are stained instantaneously. Tissues can be viewed by fluorescence microscopy immediately after perfusion. The staining is remarkably bright with very low background so that high contrast images can be obtained using objective lenses of different magnification powers.

The invention also provides for an animal model of ocular neovascularization. The model is discussed in detail below, but generally it is based upon the injection of material into the subretinal space of an animal's eye. Any suitable non-human animal model for ocular disease may be used, and the injected material may range from Matrigel™, an extract of extracellular matrix (ECM) proteins from the murine EHS (Engelbreth-Holm-Swarm) tumor that is widely used as reconstituted basement membrane in cell culture experiments, to a simple solution of rat tail collagen I, bovine collagen I, and human collagen I (such as that available from BD Biosciences). See Gautreau, A. et. al., PNAS, 96: 7300. (1999); Abir R. et al. Hum Reprod, 14:299.(1999); and Abir R. et al. Fertil Steril, 75:141. (2001). Other sources of collagen may be used, including those produced by using lyophilized collagen (such as rat tail collagen from Roche) dissolved in 0.1× DME pH 4.0 (DME power from Life technologies without $NaHCO_3$, make a 10× solution but with the pH color indicator, and use HCl to adjust pH to 4.0, then dilute this solution with water to make the 0.1× DME solution) and a 10% acetic acid solution.

Without being bound by theory, and offered to improve the understanding of the invention, the injection of a collagen (or protein) solution is believed to be sufficient to mimic the abnormal deposits that occur in AMD after injection into the subretinal space of rats to induce new blood vessels invasion. Such animal models may be advantageously used to screen candidate active agents of the invention for activity against angiogenesis, neovascularization (such as CNV), and AMD. Non-limiting examples of such methods include those comprising the administration (by any method disclosed herein) of a candidate agent to said animal and determining the effect (increase, decrease, or no change) on angiogenesis or neovascularization in said animal.

The following examples are put forth so as to provide those of ordinary skill in the art with a complete disclosure and description of how to make and use the present invention, and are not intended to limit the scope of what the inventors regard as their invention nor are they intended to represent that the experiments below are all and only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Matrigel™ Based Animal Model

Within this application, unless otherwise stated, the techniques utilized may be found in any of several well-known references, such as: *Molecular Cloning: A Laboratory Manual* (Sambrook et al., Cold Spring Harbor Laboratory Press (1989); "Guide to Protein Purification" in *Methods in Enzymology* (M. P. Deutshcer, ed., (1990) Academic Press, Inc.); *Culture of Animal Cells: A Manual of Basic Technique*, 2nd Ed., Liss, Inc., New York, N.Y., (1987).

In search of effective treatments for CNV, a simple animal model was created by injecting 2-3.mu.l Matrigel™ to the subretinal space of adult Sprague-Dawley rats using a 33-gauge needle connected to a 10.mu.l Hamilton microsyringe. A week or more later the animals were sacrificed by $CO.sub.2$ inhalation and perfused with Vessel Paint, a new visualization technique recently developed in the inventors' lab that enables screening agents, including chemical compounds and proteins, for their potential in inhibiting CNV (Wen, ARVO Abstract, March 2002). Vessel Painting comprises the use of a solution containing DiI, followed by 4% paraformaldehyde solution, and is discussed further below.

The anterior portion of the eye, including the cornea and lens, was removed, and the eyecup was imbedded in 5% agarose. Serial thick sections (100.mu.m) of the eye were cut on a vibratome and mounted on glass slides. Eye sections were examined by fluorescence microscopy for neovascularization in the Matrigel™ deposit. Serial optical sections were obtained using confocal microscopy. Three-dimensional reconstruction of newly developed blood vessels was achieved using Auto Visualiz-3D (Autoquant Imaging, Inc.). Protein leakage of the new vessels was detected by assessing color change in the Matrigel™ deposit after intravenous injection of Evan's Blue dye.

Neovascularization was observed as early as 7 days after Matrigel™ injection, and extensive CNV was evident 10 days after Matrigel™ injection in all of the eyes injected. New blood vessels, originated from choriocapillaris exclusively, invaded the Matrigel™ deposit and formed extensive networks 14 days after Matrigel™ injection. Three-dimensional reconstruction clearly showed that the new vessels originated from the choroid. The Matrigel™ deposit became light blue in color after Evan's blue injection, as compared with pale white surrounding tissue, indicating the lack of barrier. Disciform scar was observed 30 days after Matrigel™ injection.

Thus, the subretinal Matrigel™ deposits induce CNV in the subretinal space, mimicking the pathology seen in exudative, or wet form, AMD, and thereby providing an improved animal model for researching the pathology of CNV and for testing potential therapies.

Example 2

Inhibition of CNV

In the initial characterization of the model, it was suspected that there was a possible involvement of an inflammatory reaction to Matrigel™ in the generation of neovascularization. As a result, two known immunosuppressants were tested, cyclosporin and rapamycin.

Oral administration of cyclosporin (15 mg/kg/d, given 4 days before Matrigel™ injection thorough 10 days after injection) had no effect on CNV. In marked contrast, however, oral rapamycin (Rapamune®, 1.5 mg/kg/d, given 4 days before Matrigel™ injection thorough 10 days after injection) resulted in complete inhibition of CNV development in the 16 eyes tested. Rapamycin is commercially available as oral solution, marketed as Rapamune Oral Solution by Wyeth-Ayerst. Thus, the anti-CNV properties of rapamycin by local administration were further examined.

Since rapamycin is not soluble in water, it was either dissolved in DMSO (tested in 8 eyes) or suspended in PBS (tested in 6 eyes), then mixed with Matrigel™. The mixed Matrigel™-containing rapamycin was injected to the subretinal space. At a dose of 25 rapamycin (or 30 μg/injection, since each injection used 1.2 μl of Matrigel™), there was again a complete inhibition of CNV in rapamycin-treated eyes.

In further experiments, and using the methods described above, the amount of rapamycin was reduced to 2.5 μg/μL. At this amount (the word "concentration" is not being used since rapamycin is not soluble in water), the crystals of rapamycin were clearly visible, even after 10 days. In each case, there was no detectable neovascularization in treated eyes. Concerns with insolubility, if they exist, may be addressed by the use of soluble active agents of the invention, such as, but not limited to, SDZ-RAD.

Rapamycin thus has the potential to inhibit or prevent CNV in human patients. In addition, local administration of rapamycin is evidently a practical approach to CNV treatment, which is particularly advantageous given the potential disadvantages effects of systemic administration.

Example 3

Vessel Painting

The retina from a normal 3 months old Sprague-Dawley rat, sacrificed by $CO_2$ overdose was perfused with Vessel Paint (DiI, 0.1 mg/ml), followed by 4% paraformaldehyde. The retina was dissected and postfixed in the same fixative for 1 hr, rinsed in phosphate buffered saline (PBS), and flat-mounted on glass slides. Microphotographs were taken on a Nikon E800 microscope.

Microphotographs of the flat-mount retina showed that vessels stain brightly with a low background. Endothelial cell nuclei were also stained and easily identifiable. The spatial structure of the vasculature was well preserved and the deep retinal capillaries were also visible.

The vascular network is better appreciated by images to show its three-dimensionality. Excellent 3-D images of vasculature can be obtained using the corrosion-casting technique and scanning electron microscopy (SEM), see Konerding M A (1991) Scanning electron microscopy of corrosion casting in medicine. *Scanning Microsc.* 5:851-865. However, corrosion casting is technically challenging and time-consuming, as is SEM. Alternatively, 3-D images can be reconstructed from a stack of serial optical sections by confocal microscopy. Bright staining and a high signal-to-noise ratio by Vessel Painting make it possible to obtain serial optical sections of samples as thick as 100-150 μm by laser scanning confocal microscopy without significant deterioration of signal from the bottom of the sample even using objective lenses of low magnification power. High quality of 3-D images at different viewing angles can be reconstructed from a stack of 2-D digital images using commercially available software. FIG. 1 shows 3-D reconstructed images of a flat-mounted retina, processed as described above. A stack of 78 optical sections along the Z-axis (z-step=1 μm) was taken by confocal microscopy using a 20× objective lens on a Bio-Rad MRC-1024 confocal microscope. Three-D images were reconstructed to show the retinal vasculature at an angle of 0° (FIG. 1A) or 180° (FIG. 1B). Both depict an artery on the retinal surface with connections to the deep capillaries.

Example 4

CNV in Matrigel™ Injected Area

Matrigel™ is an extract of extracellular matrix (ECM) proteins from the murine EHS (Engelbreth-Holm-Swarm) tumor and is widely used as reconstituted basement membrane in cell culture experiments. It is also used to assess angiogenic or antiangiogenic agents in an in vivo assay, the Matrigel™ plug assay (Passaniti A, Taylor R M, Pili R, et al. (1992) A simple, quantitative method for assessing angiogenesis and antiangiogenic agents using reconstituted basement membrane, heparin, and fibroblast growth factor. *Lab Invest.* 67:519-528). Pathological studies indicate an association between CNV and abnormal deposits of extracellular matrix (ECM) in the location between the retinal pigment epithelium (RPE) and Bruch's membrane. In order to mimic the abnormal deposits that occur in AMD, Matrigel™ was injected into the subretinal space of rats. New blood vessels invade Matrigel™ deposits shortly after Matrigel™ injection.

In the following, Matrigel™ (1.2 µl) was introduced to the subretinal space by injection into eyes of Sprague-Dawley rats. At a given time after injection, the animal was sacrificed and perfused with Vessel Paint, followed by 4% paraformaldehyde solution. The anterior portion of the eye was removed and the eyecup was then embedded in 5% agarose. Serial cross sections (100 µm thick) were cut on a vibratome.

New blood vessels originating from the choriocapillaris were detectable as early as 4 days after Matrigel™ injection and became well developed by 10 days after injection. A DIC image of a cross section of an eye, from a 2 month old animal 10 days after Matrigel™ injection, is shown in FIG. 2A. The DIC image was superimposed with an optical section to show CNV along with choroidal and retinal vasculature (FIG. 2A). New blood vessels penetrate Bruch's membrane at a single site (yellow arrowhead) and then ramify in the Matrigel™ layer between the RPE and the retina. A stack of 42 optical sections were taken from this sample and a 3-D image was reconstructed (FIG. 2B). The 3-D image clearly shows that the new blood vessels originated from the choriocapillaris through a single penetration site (yellow arrowhead).

The permeability of newly formed blood vessels was assessed by Evans Blue assay. Evans Blue (60 mg/kg in PBS) was injected intravenously to a Sprague-Dawley rat whose eyes had been injected with Matrigel™ 10 days before. A choroid-retina preparation was dissected, flat-mounted and viewed by fluorescence microscopy. Evans Blue staining was only seen in the Matrigel™ injected area, indicating the leaky nature of the new vessels.

Example 5

Inhibition of CNV by Rapamycin

In initial screens of potential anti angiogenic agents using the Matrigel™ model, rapamycin demonstrated a remarkable ability to inhibit new blood vessel formation. Rapamycin, clinically used as immunosuppressant (Kahan B D (2001) Sirolimus: a comprehensive review. *Expert Opin. Pharmacother.* 2:1903-1917), binds to a FKBP (FK506 binding protein) to form an FKBP-rapamycin complex, which in turn inhibits the function of mTOR (mammalian target of rapamycin), a central controller of cell growth (Schmelzle T, Hall M N (2000) TOR, a central controller of cell growth. *Cell* 103:253-262). Rapamycin inhibits endothelial cell proliferation (Vinals F, Chambard J C, Pouyssegur J (1999) p70 S6 kinase-mediated protein synthesis is a critical step for vascular endothelial cell proliferation. *J. Biol. Chem.* 274:26776-26782) and the response to VEGF (Yu Y, Sato J D (1999) MAP kinases, phosphatidylinositol 3-kinase, and p70 S6 kinase mediate the mitogenic response of human endothelial cells to vascular endothelial growth factor. *J. Cell Physiol.* 178:235-246) and bFGF (basic fibroblast growth factor) and PDGF (platelet-derived growth factor). See Cao et al. (1995) Effects of rapamycin on growth factor-stimulated vascular smooth muscle cell DNA synthesis. Inhibition of basic fibroblast growth factor and platelet-derived growth factor action and antagonism of rapamycin by FK506. *Transplantation* 59(3):390-5 and Ruygrok et al. (2003) Rapamycin and cardiovascular medicine. *Intern. Med. J.* 33(3):103-9. It has been shown to block tumor angiogenesis (Guba M, von Breitenbuch P, Steinbauer M, et al. (2002) Rapamycin inhibits primary and metastatic tumor growth by antiangiogenesis: involvement of vascular endothelial growth factor. *Nat. Med.* 8:128-135).

Figure 2:
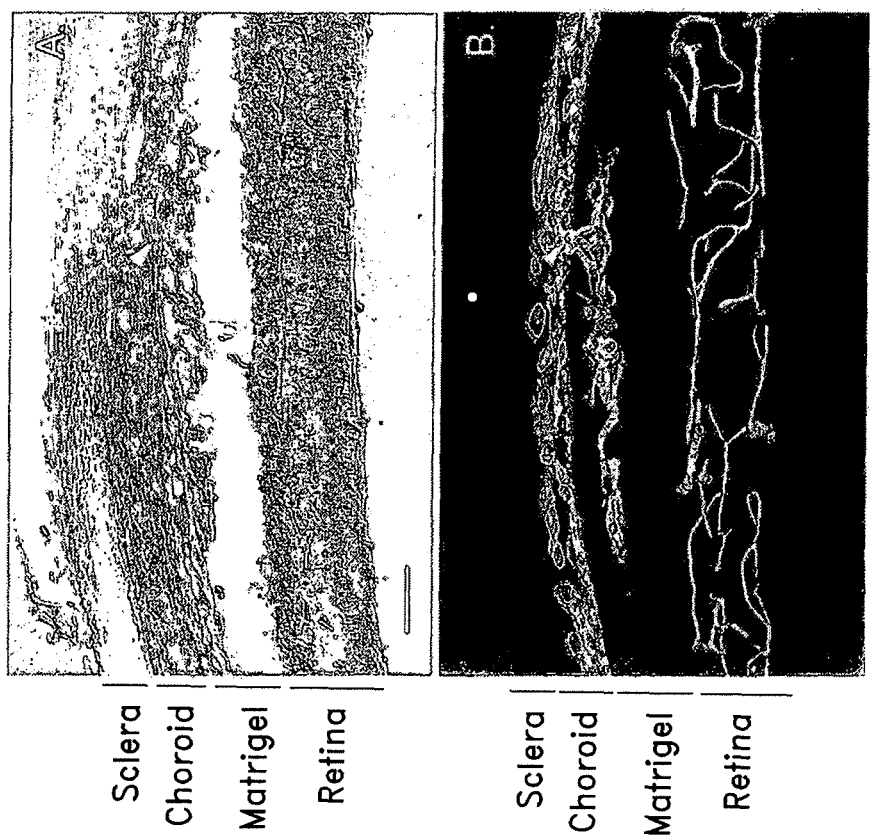
FIG. 2 shows CNV in tissue from a Matrigel injected eye. Scale bar: 100 μm.

Adult Sprague-Dawley rats (n=22) were injected with Matrigel™ to the subretinal space. Animals were fed with rapamycin once a day at a dose of 3 mg/kg started 4 days before Matrigel™ injection. Eyes were collected at 10 days (n=18) or 20 days (n=4) after Matrigel™ injection and processed as described in Example 4. Tissue sections were examined by fluorescence microscopy. None of the eyes collected at 10 days contained any new blood vessels invading the subretinal space in rapamycin treated animals. In the 20 days group, some newly formed blood vessels started to invade the Matrigel™ area. The amount of CNV in this group was semi-quantified as (+). In comparison, CNV in control animals (10 days) were graded as (+++~++++), as shown in FIG. 2.

In another group of animals, rapamycin was mixed with Matrigel™ (suspension, 1 µg/µl, n=6; 10 µg/µl, n=11) and co-injected to the subretinal space with Matrigel™ (in-gel delivery). Eyes were collected 10 days after injection and processed as described in Example 4. No CNV was found in any of the eyes treated with rapamycin by in-gel delivery. FIG. 3 shows a DIC image of a section from an eye, injected with Matrigel and rapamycin mixture at a high dose (10 µg/µl suspension) 10 days before tissue collection, to show rapamycin particles in the subretinal space. Rapamycin particles in Matrigel™ are clearly seen in the DIC image, which is superimposed on a confocal image of Vessel Paint staining to show the choroidal and retinal blood vessels. No CNV was found in any eyes injected with rapamycin.

In all experiments, rapamycin had no discernable effect on the normal vasculature of the eye. Cyclosporin, also an immunosuppressant, failed to inhibit CNV formation either when administrated orally (100 mg/kg/d, n=3) or in-gel (25 µg/µl, n=3) by the same experimental paradigm.

Example 5

CNV Index in FK506 Tacrolimus Treated Eyes

FK506, which is not water soluble, was mixed with Matrigel™ (as a suspension) at 10 µg/µl, and 1.2 µl were injected into the subretinal space as described above. Eyes were collected 10 days after injection and blood vessels were stained with Vessel Paint. Eyes were embedded in 5% agarose and serial sections were cut (100 µm thick) on a vibratome. CNV was examined by fluorescence microscopy and CNV index of each eye was calculated. Results are shown below.

| FK506 | Mean = 12.67 (n = 6) | SEM = 2.76 |
|---|---|---|
| Control | Mean = 32.00 (n= 10) | SEM = 6.41 |
| Student's t-test | P = 0.042 | |

Therefore, FK506 inhibited CNV by 60%.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of administration of an ophthalmic formulation, comprising administering the ophthalmic formulation to a human by placement of the formulation into the vitreous or by placement of the formulation between the conjunctiva and the sclera of an eye of the human, wherein the formulation comprises rapamycin and a second component comprising polyethylene glycol.

2. The method of claim 1, wherein the second component further comprises ethanol.

3. The method of claim 1, wherein the formulation is a solution of rapamycin dissolved in the second component.

4. The method of claim 1, wherein the formulation is a suspension of rapamycin in the second component.

5. The method of claim 1, wherein the formulation contains an amount of rapamycin effective to treat the wet form of age-related macular degeneration in a human.

6. The method of claim 1, wherein the formulation comprises between 0.25% (w/w) to 2.5% (w/w) of rapamycin.

7. The method of claim 1, wherein the administering is done by placement of the formulation into the vitreous.

8. The method of claim 1, wherein the administering is done by placement of the formulation between the conjunctiva and the sclera.

9. A method of administration of an ophthalmic formulation, comprising intravitreal or subconjunctival injection of the ophthalmic formulation into an eye of a human, wherein the formulation comprises polyethylene glycol and an agent selected from the group consisting of rapamycin, tacrolimus, everolimus, pimecrolimus, and temsirolimus.

10. The method of claim 9, wherein the agent is selected from the group consisting of rapamycin and tacrolimus.

11. The method of claim 9, wherein the agent is selected from the group consisting of rapamycin, everolimus, and temsirolimus.

12. The method of claim 9, wherein the agent is rapamycin.

13. The method of claim 9, wherein the formulation further comprises ethanol.

14. The method of claim 9, wherein the formulation is a solution of the agent dissolved in the polyethylene glycol.

15. The method of claim 9, wherein the formulation is a suspension of the agent in the polyethylene glycol.

16. The method of claim 9, wherein the formulation contains an amount of the agent effective to treat the wet form of age-related macular degeneration in the human.

17. The method of claim 9, wherein the composition comprises between 0.25% (w/w) to 2.5% (w/w) of rapamycin.

18. The method of claim 9, comprising the intravitreal injection of the ophthalmic formulation.

19. The method of claim 9, comprising the subconjunctival injection of the ophthalmic formulation.

20. A method of administration of an ophthalmic formulation, comprising intravitreal injection of the ophthalmic formulation into an eye of a human, wherein the formulation comprises rapamycin and a second component comprising polyethylene glycol.

21. The method of claim 20, wherein the formulation comprises between 0.25% (w/w) to 2.5% (w/w) of rapamycin.

* * * * *